United States Patent [19]

Sims

[11] Patent Number: 5,120,124
[45] Date of Patent: Jun. 9, 1992

[54] DEVICES FOR DETERMINING THE CROSSED CYLINDER POWERS AND AXES FOR MULTIPLE LENS SETS

[76] Inventor: Clinton N. Sims, 3432 W. Riverside Dr., Ft. Myers, Fla. 33901

[21] Appl. No.: 526,395

[22] Filed: May 21, 1990

Related U.S. Application Data

[63] Continuation-in-part of Ser. No. 427,724, Oct. 27, 1989, which is a continuation-in-part of Ser. No. 310,334, Feb. 13, 1989, Pat. No. 4,943,162, which is a continuation-in-part of Ser. No. 116,322, Nov. 2, 1987, Pat. No. 4,840,479, which is a continuation-in-part of Ser. No. 23,980, Mar. 16, 1987, Pat. No. 4,820,040, which is a continuation of Ser. No. 670,398, Nov. 9, 1984, abandoned.

[51] Int. Cl.$^5$ .............................. A61B 3/02
[52] U.S. Cl. ................... 351/235; 351/234
[58] Field of Search .............. 351/227, 228, 229, 230, 351/231, 233, 234, 235, 246

[56] References Cited

U.S. PATENT DOCUMENTS

| | | |
|---|---|---|
| 579,132 | 3/1897 | Clark . |
| 1,222,017 | 4/1917 | Moseley . |
| 1,266,224 | 5/1918 | Day . |
| 1,337,265 | 4/1920 | Poser . |
| 1,550,582 | 8/1925 | Sheard . |
| 1,594,196 | 7/1926 | Herold et al. . |
| 1,611,167 | 12/1926 | De Zeng ........................ 351/235 |
| 1,794,571 | 3/1931 | Wrighton et al. . |
| 2,147,448 | 2/1939 | Lee . |
| 2,256,491 | 9/1941 | Peck et al. . |
| 2,333,738 | 11/1943 | Peck et al. . |
| 2,874,610 | 2/1959 | Wright . |
| 2,923,200 | 2/1960 | Wright . |
| 2,938,426 | 5/1960 | Armbruster et al. . |
| 2,968,213 | 1/1961 | Wright et al. . |
| 2,995,065 | 8/1961 | Wright et al. . |
| 3,015,988 | 1/1962 | Hemstreet . |
| 3,136,839 | 6/1964 | Safir . |
| 3,415,594 | 12/1968 | Aulhorn . |
| 3,428,398 | 2/1969 | Gottschalk . |
| 3,498,699 | 3/1970 | Wilkinson . |
| 3,524,702 | 8/1970 | Bellows et al. . |
| 3,572,908 | 3/1971 | Grolman . |
| 3,602,580 | 8/1971 | Samuels . |
| 3,664,631 | 5/1972 | Guyton . |
| 3,785,723 | 1/1974 | Guyton . |
| 3,791,719 | 2/1974 | Kratzer et al. . |
| 3,819,256 | 6/1974 | Bellows et al. . |
| 3,822,932 | 7/1974 | Humphrey . |
| 3,832,066 | 8/1974 | Cornsweet . |
| 3,841,760 | 10/1974 | Guyton . |
| 3,860,330 | 1/1975 | Persson . |

(List continued on next page.)

FOREIGN PATENT DOCUMENTS 598683 5/1960 Canada .
820766 9/1959 United Kingdom .

OTHER PUBLICATIONS

Stokes, "On a Mode Measuring the Astigmatism of a Defective Eye", (1983).

(List continued on next page.)

*Primary Examiner*—Rodney B. Bovernick
*Attorney, Agent, or Firm*—Kilpatrick & Cody

[57] ABSTRACT

Apparatus and techniques for measuring and determining the crossed cylinder powers and axes obtained through independent rotation of cylinder lenses are disclosed. Degree scales associated with each lens provide angular measurements for use in connection with a chart or similar apparatus, and in some embodiments determination of the resulting crossed cylinder powers and angles made be made directly from markings included on alternatively designed scales. Unlike many other refractive devices, however, which require use of a digital computer to determine the resulting crossed cylinder power and axis of multiple lenses, the present invention allows such a determination to be made merely by manipulating the positions of the lenses (and viewing entries on the chart as appropriate) and performing simple mathematical operations on the values obtained.

5 Claims, 3 Drawing Sheets

U.S. PATENT DOCUMENTS

| | | |
|---|---|---|
| 3,874,774 | 4/1975 | Humphrey . |
| 3,880,502 | 4/1975 | Humphrey . |
| 3,883,233 | 5/1975 | Guilino . |
| 3,969,020 | 7/1976 | Lynn et al. . |
| 4,021,102 | 5/1977 | Iizuka . |
| 4,105,302 | 8/1978 | Tate, Jr. . |
| 4,179,196 | 12/1979 | Persson et al. . |
| 4,180,323 | 12/1979 | Persson et al. . |
| 4,185,896 | 1/1980 | Buhler . |
| 4,190,332 | 2/1980 | Body et al. . |
| 4,215,919 | 8/1980 | Rybicki . |
| 4,385,813 | 5/1983 | Klein et al. . |
| 4,413,891 | 11/1983 | Rybicki . |
| 4,426,140 | 1/1984 | Stephens . |
| 4,436,390 | 3/1984 | Aoki . |
| 4,496,226 | 1/1985 | Augusto et al. . |
| 4,523,822 | 6/1985 | Thurston . |
| 4,606,524 | 8/1986 | Wood . |

OTHER PUBLICATIONS

Dennett, "The Stokes' Lens for Measuring Astigmatism", (1985).

Jackson, "A Trail Set of Small Lenses in a Modified Trial Frame", (1987).

"Dr. Thomson's 1895 Correspondence Course in Optics with Historical Commentary by Monroe J. Hirsch".

Friedman, "The Jackson Crossed Cylinder, A Critique", (1940).

Crisp, "A New Cross-Cylinder Test for Astigmatic Axis, Without Use of Test Type", (1942).

Littman, "Fundamental Considerations about Opthalmometry", (1951).

Wunsh, "The Crossed Cylinder", (chapter 38 of Clinical Ophthalmology, (vol. 1), Duane, editor, (1978).

Kaufman, "Subjective Refraction: Fogging Use of the Astigmatic Dials", (chapter 39 of Clinical Ophthalmology, (vol. 1), Duane, editor, (1978).

Duke-Elder and Abrams, "Opthalmic Optics in Refraction", (1970), pp. 438-439.

Alverez, "Development of Variable—Focus Lenses and a New Refractor", (1978).

Michaels, Visual Optics and Refraction, (chapter 12), (1980).

Guyton, "Automated Clinical Refraction", (chapter 67 of Clinical Ophthalmology, (vol. 1)), edition 1985.

Chapter 67 of "Clinical Opthalmology", vol. 1, by Duane and Jaeger (1986).

Page 12263 of "The American Encyclopedia and Dictionary of Opthalmology", vol. 16, edited by Wood (1920).

Pages 7195-7197 of "The American Encyclopedia and Dictionary of Ophthalmology", vol. 10, edited by Wood (1917).

Page 438 in vol. 5 of "System of Ophthalmology", entitled *Ophthalmic Optics and Refraction,* by Duek-Elder and Agrams (1970).

Pages 449-465 of "System of Diseases of the Eye", vol. 4, edited by Norris and Oliver (1900).

Chapters V and VIII-XII of Thorington, *Refraction and How to Refract*, P. Blakiston's Son & Co. (1900).

| C | RESULTANT Dp | X/CYL ~54 Da |
|---|---|---|
| °90° | -1.50 | +3.00 x 90° |
| +85° (-95°) | -1.50 | +3.00 x 92° |
| +80° (-100°) | -1.50 | +3.00 x 95° |
| +75° (-105°) | -1.50 | +3.00 x 97° |
| +70° (-110°) | -1.37 | +2.75 x 100° |
| +65° (-115°) | -1.37 | +2.75 x 102° |
| +60° (-120°) | -1.25 | +2.50 x 105° |
| +55° (-125°) | -1.25 | +2.50 x 107° |
| +50° (-130°) | -1.12 | +2.25 x 110° |
| +45° (-135°) | -1.12 | +2.25 x 112° |
| +40° (-140°) | -1.00 | +2.00 x 115° |
| +35° (-145°) | -0.87 | +1.75 x 117° |
| +30° (-150°) | -0.75 | +1.50 x 120° |
| +25° (-155°) | -0.62 | +1.25 x 122° |
| +20° (-160°) | -0.50 | +1.00 x 125° |
| +15° (-165°) | -0.37 | +0.75 x 128° |
| +10° (-170°) | -0.25 | +0.50 x 130° |
| + 5° (-175°) | -0.12 | +0.25 x 135° |
| 0° (±180°) | 00 | |
| - 5° (+175°) | -0.12 | +0.25 x 45° |
| - 10° (+170°) | -0.25 | +0.50 x 50° |
| - 15° (+165°) | -0.37 | +0.75 x 51° |
| - 20° (+160°) | -0.50 | +1.00 x 55° |
| - 25° (+155°) | -0.62 | +1.25 x 57° |
| - 30° (+150°) | -0.75 | +1.50 x 60° |
| - 35° (+145°) | -0.82 | +1.75 x 62° |
| - 40° (+140°) | -1.00 | +2.00 x 65° |
| - 45° (+135°) | -1.12 | +2.25 x 67° |
| - 50° (+130°) | -1.12 | +2.25 x 70° |
| - 55° (+125°) | -1.25 | +2.50 x 72° |
| - 60° (+120°) | -1.25 | +2.50 x 75° |
| - 65° (+115°) | -1.25 | +2.50 x 77° |
| - 70° (+110°) | -1.37 | +2.75 x 80° |
| - 75° (+105°) | -1.50 | +3.00 x 82° |
| - 80° (+100°) | -1.50 | +3.00 x 85° |
| - 85° (+ 95°) | -1.50 | +3.00 x 87° |
| ±90° | -1.50 | +3.00 x 90° |

FIG 3

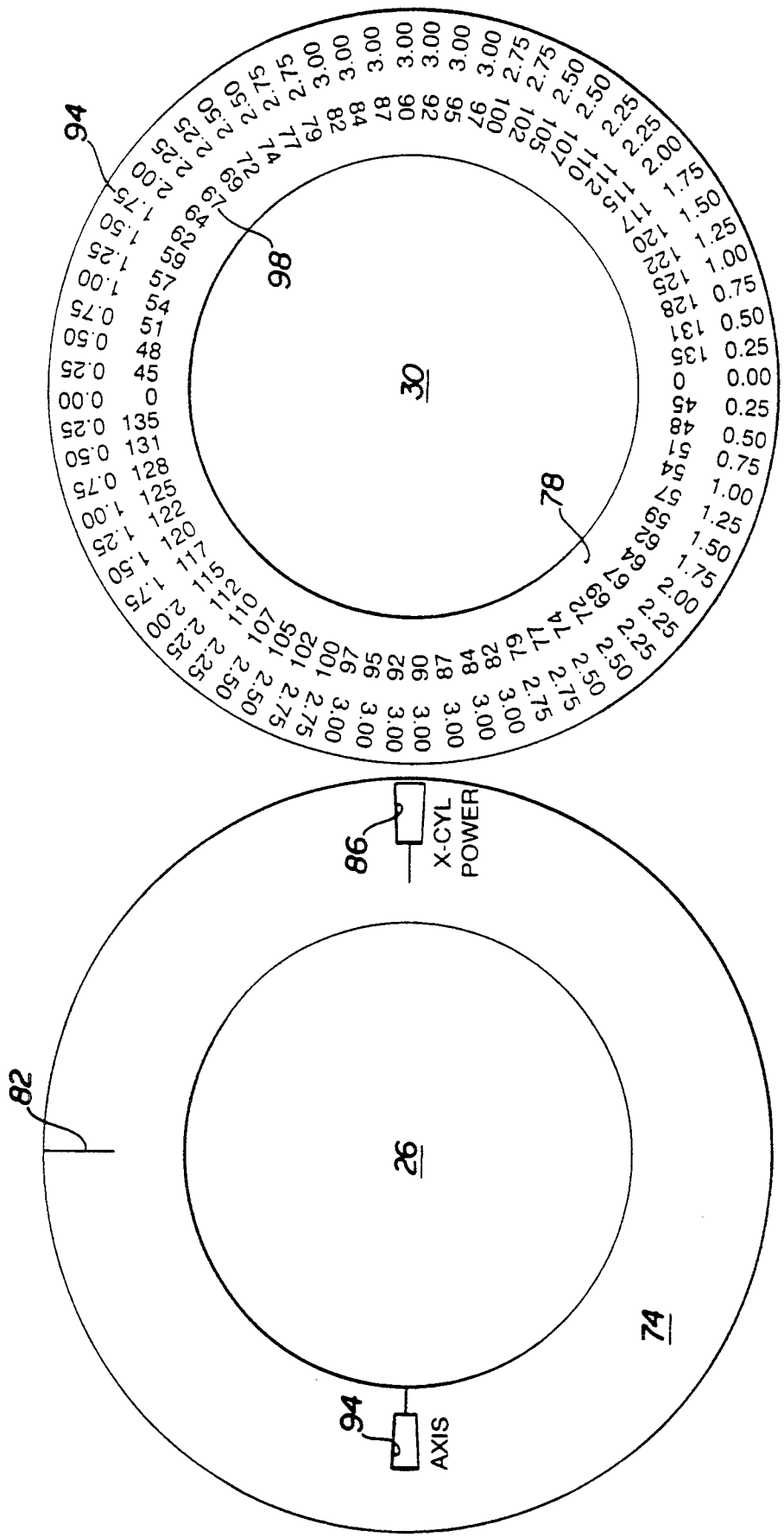

DEVICES FOR DETERMINING THE CROSSED CYLINDER POWERS AND AXES FOR MULTIPLE LENS SETS

CROSS-REFERENCE TO RELATED APPLICATIONS

This application is a continuation-in-part of application Ser. No. 07/427,724, filed Oct. 27, 1989, entitled "Trial Frames, Adjustable Spectacles and Associated Lens Systems", which application is a continuation-in-part of application Ser. No. 07/310,334 (now U.S. Pat. No. 4,943,162), filed Feb. 13, 1989, entitled "Astigmatic Self-Refractor and Method of Use", which application is a continuation-in-part of application Serial No. 07/116,322 (now U.S. Pat. No. 4,840,479), filed Nov. 2, 1987, entitled "Crossed Cylinder Lenses Refractor with Three-lens Variable Crossed Cylinder Assembly and Method of Use", which application is a continuation-in-part of application Ser. No. 07/023,980 (now U.S. Pat. No. 4,820,040) "Lenses Refractor and Method of Use", which application is a continuation of application Serial No. 06/670,398, filed Nov. 9, 1984, all of which applications are incorporated herein in their entireties by this reference.

FIELD OF THE INVENTION

This invention relates to subjective means and associated apparatus such as trial frames and refractors for measuring or determining optical errors in the eyes of humans.

SUMMARY OF THE INVENTION

Copending patent application Ser. No. 07/427,724 discloses trial frames having two independently rotatable cells alignable with each eye. Each cell is designed to house either a cylinder, polarized, prism, crossed cylinder or sphero-cylinder lens depending on the results sought to be achieved. Using two independently rotatable cylinder lenses in the two cells, for example, allows generation of varying crossed-cylinder powers throughout the entire visual field for measuring or correcting astigmatism. Polarized lenses may be used with the trial frames to detect macular defects, while a single pair of prism lenses may be used to detect and neutralize diplopia. If desired, the trial frames may include accessory clips for positioning additional lenses of any type in the patient's line-of-sight.

The trial frames described in application Ser. No. 07/427,724 offer at least two distinct advantages over existing frames. First, they allow patients to determine the appropriate astigmatic refractive or other optical correction for each eye merely by independently and alternatively rotating each of a pair of lenses. This process, akin to tuning a radio receiver, provides a reliable method for subjectively ascertaining the correction necessary without resort to batteries of trial lenses. Successful neutralization of refractive error by alternative independent rotation of lenses is a surprising result, as the rotation changes both the resulting power and axis, contrary to the result achieved through counter-rotation of lenses. Second, because the lens system used in conjunction with the novel trial frames differs from those requiring counter-rotation of various lenses, no synchronized gear system is needed for the present invention. The absence of synchronized gearing decreases the manufacturing cost, complexity, and weight of the trial frames described.

The present invention comprises apparatus and techniques for measuring and determining the crossed cylinder powers and axes obtained through independent rotation of cylinder lenses contained within the cells. In one embodiment of the invention, degree scales associated with each lens provide angular measurements for use in connection with a chart or similar apparatus. Other embodiments omit use of the chart and allow determination of the resulting crossed cylinder powers and angles directly from alternatively designed scales. Unlike many other refractive devices, however, which require use of a digital computer to determine the resulting crossed cylinder power and axis of multiple lenses, the present invention allows such a determination to be made merely by manipulating the positions of the lenses and either viewing appropriate entries on a chart or performing simple mathematical operations on the values obtained. The apparatus and techniques described also may be used in connection with refractors containing independently rotatable cylinder lenses, as well as in any other appropriately configured devices performing similar functions.

It is therefore an object of the present invention to provide devices and techniques for permitting determination of the crossed cylinder powers and axes obtained through independent rotation of multiple lenses.

It is an additional object of the present invention to provide devices and techniques for permitting determination of resulting crossed cylinder powers and axes using a degree scale associated with each rotatable lens.

It is another object of the present invention to provide devices and techniques for permitting determination of resulting crossed cylinder powers and axes using a chart or similar apparatus in conjunction with degree scales associated with the rotatable lenses.

It is yet another object of the present invention to provide devices and techniques for permitting determination of resulting crossed cylinder powers and axes without resort to use of a digital computer.

Other objects, features, and advantages of the present invention will become apparent with reference to the remainder of the written portion and the drawings of this application.

BRIEF DESCRIPTION OF THE DRAWINGS

FIG. 3 is a front view of a chart which may be used in connection with the trial frames of FIG. 1.

FIG. 4A-B is a front view of each of an alternate pair of independently rotatable lens cells which may form part of trial frames similar to those described in application Ser. No. 7/427,724.

DETAILED DESCRIPTION OF THE DRAWINGS

Figure 1:
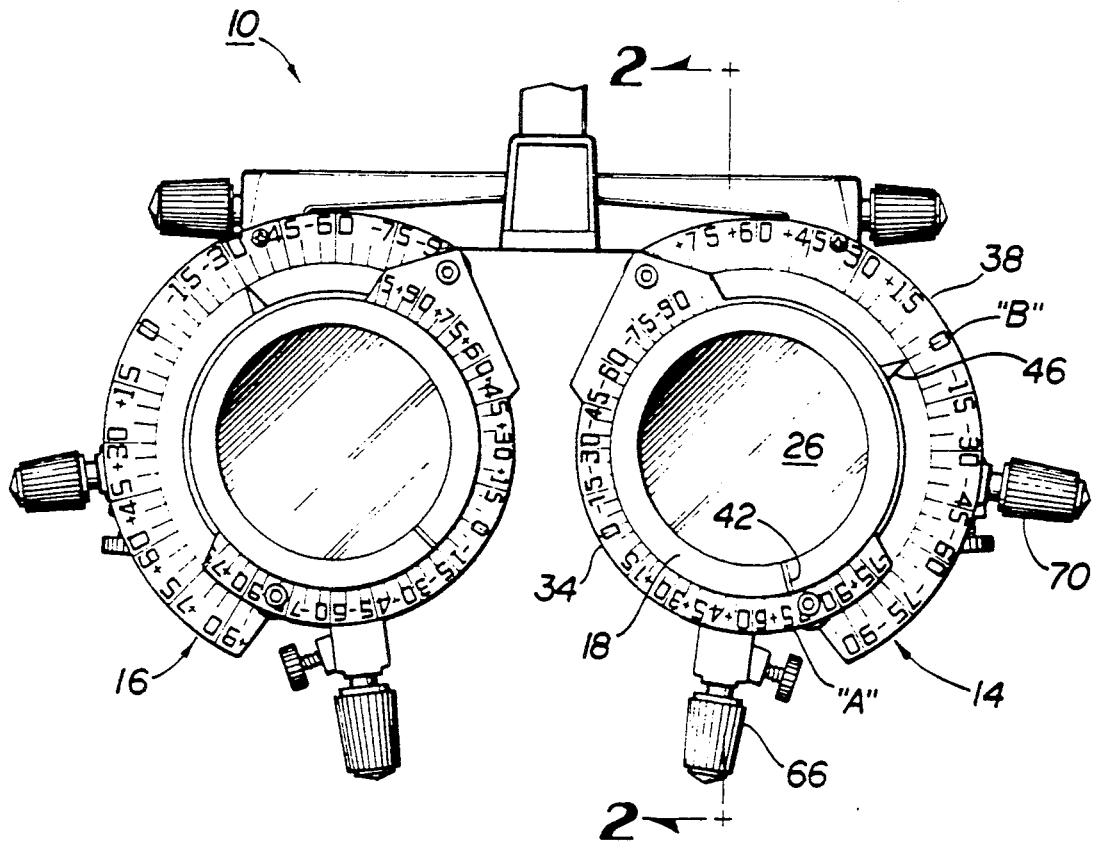
FIG. 1 is a front elevational view of trial similar to those described in application Ser. No. 07/427,724 illustrating the rotatable lens cells and degree scales used in connection with the present invention.

FIG. 1 illustrates trial frames 10 comprising a right eye frame 14 and a left eye frame 16 (with "right" and "left" determined from the refractionist's point of view), which eye frames may be essentially mirror images. Trial frames 10 need only include one eye frame, however, as only one eye need be refracted at a time. Because the right and left eyes may be refracted separately and the internal structure of right and left eye frames 14 and 16 are essentially identical, only the structure of right eye frame 14 will be described in the text of this application. Trial frames 10 are, however, described in greater detail in copending application Ser. No. 07/427,724, which application has been incorporated herein by reference, and those having ordinary skill in the art may refer to that application for additional information if desired.

Figure 2:
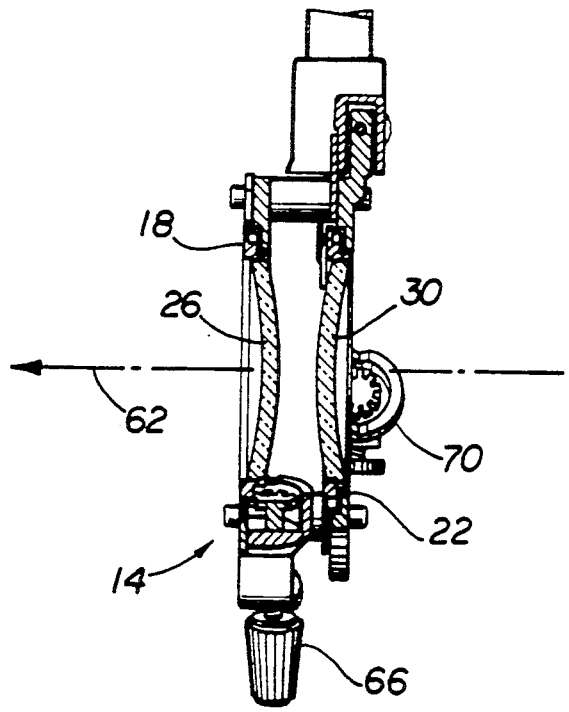
FIG. 2 is a side elevational view of a pair of the independently rotatable lens cells which form part of the trial frames of FIG. 1.

As shown in FIG. 2, right eye frame 14 includes two independently rotatable lens cells 18 and 22. Frame 14 also may include cylinder lenses 26 and 30 in each of cells 18 and 22, respectively, and degree scales 34 and 38 (FIG. 1). Scales 34 and 38 correspond to lenses 26 and 30 and may be used to determine the angular deviation of the respective lenses from neutral positions, thereby providing information from which the patient's optimal optical prescription may be derived.

FIGS. 1-2 detail lens cells 18 and 22 and their associated degree scales 34 and 38. Lens cell 18 includes pointer 42 extending to its periphery. Pointer 42 corresponds to degree scale 34, which divides the periphery of lens cell 18 into 360 equal segments (i.e. 360°) and may be printed in 5° increments as illustrated on or otherwise secured to trial frames 10 so that rotation of lens cell 18 alters the position of the pointer 42 relative to a given portion of the degree scale 34. Lens cell 22 includes pointer 46 and degree scale 38, which similarly divides cell 22 into 360 equal segments (i.e. 360°) around its periphery as shown in FIG. 1. By appropriately positioning the major axes of lenses 26 and 30 in cells 18 and 22, degree scales 34 and 38 need extend only approximately 180° around the respective peripheries of cells 18 and 22, permitting both scales 34 and 38 to be positioned with little or no overlap and easily observed as cells 18 and 22 are rotated during the refraction process.

FIG. 3 illustrates card or chart 50 which may be used in connection with the present invention. Chart 50 details intermediate crossed-cylinder measurements, which measurements are listed in the right-hand column 54 as a function of the value of degree scales 34 and 38 corresponding to the final position of pointers 42 and 46, respectively.

Determination of a patient's astigmatic refractive error may be accomplished as follows. Using an embodiment of the invention consistent with FIGS. 1-3 and including +1.50×90° D and −1.50×90° D cylinder lenses for lenses 26 and 30, respectively, the lens cells 18 and 22 are placed in their "unrotated" positions (so that the sum of the powers of lenses 26 and 30 is 0.00 D) and trial frames 10 are worn by the patient. In the unrotated positions of lens cells 18 and 22, pointers 42 and 46 point to the respective 0° marks on degree scales 34 and 38.

The sphere lens providing the clearest vision for the patient initially may be determined (if necessary) using any appropriate technique, including, for example, conventional methods involving a refractor or variable telescopic lens device having a sphere lens assembly. The appropriate sphere lens then may be placed in an accessory clip associated with trial frames 10, if one is present, or the patient may be instructed to continue looking through the refractor or similar device. Once the most satisfactory sphere power is determined and positioned in line-of-sight 62, the patient may merely rotate knobs 66 and 70 of trial frames 10 independently and alternatively until the best visual acuity is achieved. Rotating knobs 66 and 70 alters the positions of lenses 26 and 30 in lens cells 18 and 22 relative to degree scales 34 and 38, respectively, and to each other.

Once the patient has rotated knobs 66 and 70 to their final positions, the degree markings of scales 34 and 38 corresponding to pointers 42 and 46 (which markings may be denoted "A" and "B" respectively) are observed and added together to form the independent variable "C" used in connection with chart 50. The crossed-cylinder entry observable in the right-hand column 54 of chart 50 opposite the value of variable "C" then may be read as dependent variable "D", which includes both the crossed cylinder power ("$D_p$") and axis ("$D_a$") components. Once the value of dependent variable "D" is determined, the figure ("A") on degree scale 34 corresponding to the position of pointer 42 is added to axis component "$D_1$" to yield the resulting astigmatic crossed-cylinder power and axis prescription ("R") for that patient. Written symbolically:

$$R = D_p \times (D_a + A)$$

where $D_p \times D_a = f(C)$;

$C = A + B$;

$D_p$ is in crossed cylinder diopters; and $D_a$, A, and B are in degrees

Underlying the present invention is the fact that the cylinder powers generated by rotating either of lenses 26 and 30 relative to the other form a sine curve dependent on the angle of rotation. Because the amount of rotation of the lenses bears a determinable relation to the generated cylinder power, those having ordinary skill in the art will recognize that cylinder lenses of other powers and angles may be substituted for lenses 26 and 30 if appropriate modifications are made to the values contained in chart 50. Similarly, altering chart 50 allows either or both of lenses 26 and 30 to be positioned other than in the 90° meridian.

FIG. 4A-B details an alternate pair of independently rotatable lens cells 74 and 78 which may be substituted for lens cells 18 and 22 of FIGS. 1-2 or used in connection with a monocular device. Like cell 18, lens cell 74 includes a pointer 82 extending to its periphery for measuring in conjunction with scale 34 the amount of rotation of lens 26 from an initial position. Lens cell 74 also comprises, however, dual cell windows 86 and 90 through which portions of two scales 94 and 98 associated with lens cell 78 may be observed. The portion of scale 94 observable through cell window 86 defines the resultant cylinders of the crossed cylinder power of the lens combination, with values ranging from 0–3.00 D obtainable for every 90° of rotation of lens cell 78 if +1.50×90° and −1.50×90° cylinders are chosen for lenses 26 and 30. The portion of scale 98 observable through cell window 90, when added to the value pointed to by pointer 82, defines the resultant angular component of the patient's prescription. As shown in FIG. 4B, scale 98 divides lens cell 78 into 180 equal segments (i.e. 180°), with angular components varying between 45–135° available for each 180° of rotation of cell 78.

Although lens cell pairs 18 and 22 and 74 and 78 are described as forming or capable of forming part of trial frames 10, their equivalent also may be constructed, for example, as a mechanical device using a pair of rotatable "A" and "B" rings with coincident centers attached to a base. The "A" ring, equivalent to lens cell 18 or 74, may include a pointer associated with a degree scale appearing on the base of the device and a ring window through which a portion of the degree scale appearing on the "B" ring may be observed. The "B" ring also may include a pointer associated with the degree scale on the base of the device. Those having ordinary skill in the art will recognize that other calculating devices may be created which use as input quantities values obtained from the independent rotation of two lenses. Moreover, lens cell pairs 18 and 22 and 74 and 78 and their associated components need not be contained in trial frames 10 such as those illustrated in FIGS. 1-2, but rather may be included in any appropriate refractive device or attached to a refractor in the same manner as a reading rod.

The foregoing is provided for the purposes of illustration, explanation, and description of embodiments of the present invention. Modifications and adaptations to these embodiments will be apparent to those of ordinary skill in the art and may be made without departing from the scope and spirit of the invention. In particular, various changes may be made to the numerical values printed or otherwise secured to the lens cells, mechanical devices, and charts of the present invention so as to allow lenses of different powers and angles or different lenses to be used. Similarly, the devices themselves need not be limited to any particular apparatus, but rather can include any such devices capable of assisting in calculating or determining functions or relationships between independent and dependent variables.

I claim:

1. Trial frames comprising:
   a. right and left frames;
   b. a lens system mountable in each of the right and left frames, each of which lens systems comprises:
      i. a first lens having an optical axis; and
      ii. a second lens alignable with the optical axis;
   c. means for rotating the first and second lenses independently about the optical axis comprising a gear for engaging the first lens; and
   d. means for determining at least one quantity dependent on the rotation of the first and second lenses, which quantity is selected from the group consisting of (i) the angular rotation about the optical axis of at least one of the first and second lenses, (ii) the corrective power of at least one of the first and second lenses, and (iii) the corrective axis of at least one of the first and second lenses.

2. Trial frames according to claim 1 further comprising means for determining the sum of the powers of the first and second lenses for any given angle of rotation of each lens.

3. Trial frames according to claim 2 in which the sum determining means comprises a chart.

4. Trial frames comprising:
   a. right and left lens frames;
   b. a lens system mountable in each of the right and left frames, each of which lens systems comprises:
      i. a first lens having an optical axis; and
      ii. a second lens alignable with the optical axis;
   c. means for rotating the first and second lenses of each lens system independently about the optical axis comprising a gear for engaging the first lens;
   d. a first scale associated with each frame;
   e. a second scale associated with each second lens;
   f. a housing for each first lens, which housing comprises a pointer for determining in conjunction with the first scale the rotation of the first lens; and
   g. a housing for each second lens, which housing comprises a pointer for determining in conjunction with the second scale the rotation of the second lens.

5. Trial frames according to claim 4 for use by a patient having astigmatic error and further comprising a chart for determining the crossed-cylinder power and axis correction for the error, which correction can be written symbolically as "R" and defined as:

$$R = D_p \times (D_a + A)$$

where
   $D_p \times D_a = f(C)$;
   $C = A + B$;
   $D_p$ is in crossed cylinder diopters; and
   $D_a$, A, and B are in degrees,
with A being the rotation of the first lens, B being the rotation of the second lens, C being the independent variable listed on the chart, and $D_p \times D_a$ being the dependent variable listed on the chart.

* * * * *

UNITED STATES PATENT AND TRADEMARK OFFICE
CERTIFICATE OF CORRECTION

PATENT NO. : 5,120,124

DATED : June 9, 1992

INVENTOR(S) : Clinton N. Sims

Page 1 of 2

It is certified that error appears in the above-identified patent and that said Letters Patent is hereby corrected as shown below:

Cover page, right-hand column, line 16 insert --of-- after "Mode"

Page 2, left-hand column, line 24, delete "(1987)" and insert --(1887)--

Column 1, line 22, delete "4,820,040) "Lenses" and insert --4,820,040), filed March 16, 1987, entitled "Crossed Cylinder Lenses--

Column 2, line 48, insert --frames-- after "trial"

Column 3, line 52, delete "!8" and insert --18--

Column 4, line 19, delete "$D_1$" and insert --$D_a$--

Column 4, line 23, delete "$R = D_p \times (D_a + A)$" and insert --$R = D_p \times (D_a + A)$--

UNITED STATES PATENT AND TRADEMARK OFFICE
CERTIFICATE OF CORRECTION

PATENT NO. : 5,120,124
DATED : June 9, 1992
INVENTOR(S) : Clinton N. Sims

Page 2 of 2

It is certified that error appears in the above-indentified patent and that said Letters Patent is hereby corrected as shown below:

Column 6, line 35, delete "$R = D_p \ x \ (D_a + A)$" and insert --$R = D_p \ x \ (D_a + A)$--.

Signed and Sealed this

Thirty-first Day of August, 1993

BRUCE LEHMAN

Attest:

Attesting Officer

Commissioner of Patents and Trademarks